US00PP10560P

United States Patent [19]

Holtkamp, Sr.

[11] Patent Number: Plant 10,560

[45] Date of Patent: Aug. 18, 1998

[54] AFRICAN VIOLET PLANT NAMED 'MONET'

[75] Inventor: Reinhold Holtkamp, Sr., Rees-Haffen, Germany

[73] Assignee: International Plant Breeding A.G., Bern, Switzerland

[21] Appl. No.: 797,617

[22] Filed: Feb. 7, 1997

[51] Int. Cl.[6] ..... A01H 5/00

[52] U.S. Cl. ..... Plt./69.2

[58] Field of Search ..... Plt./69.2, 69.1

[56] References Cited

U.S. PATENT DOCUMENTS

P.P. 5,292 10/1984 Yoshida ..... Plt./69.1

*Primary Examiner*—James R. Feyrer
*Assistant Examiner*—Kent L. Bell
*Attorney, Agent, or Firm*—Foley & Lardner

[57] ABSTRACT

A new and distinct cultivar of African violet named 'Monet', as described and illustrated, and particularly characterized by its single violet-shaped, bi-colored flowers with unique markings of large white centers contrasting with the purplish blue petals; strong, upright flower stems that curve slightly toward the center to form a compact bouquet above the leaves; medium green, oval to heart-shaped leaves; profuse flowering; vigorous and compact growth habit; flowering 9–10 weeks after potting, and by its long lasting and non-dropping flowers.

1 Drawing Sheet

The present invention comprises a new and distinct cultivar of African violet plant, botanically known as *Saintpaulia ionantha*, and hereinafter referred to by the cultivar name 'Monet'.

The new cultivar was referred to during the breeding and selection process by the designation 1065/37 and is a product of a planned breeding program. The new cultivar was originated from a cross made by me in the controlled breeding program in Haffen, Federal Republic of Germany. The female, or seed parent was a cultivar designated 735. The male, or pollen parent was a cultivar designated 1065.

'Monet' was discovered and selected by me as a flowering plant within the progeny of the stated cross in a controlled environment in Haffen, West Germany. A sexual reproduction of the new cultivar by leaf cuttings, as performed by me at Haffen, West Germany, has demonstrated that the combination of chracteristics as herein disclosed for the new cultivar are firmly fixed and retained through successive generations of asexual reproduction.

'Monet' has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of 'Monet', which in combination distinguish this African violet as a new and distinct cultivar:

1) Strong, upright flower stems curving slightly toward the center.

2) Single violet-shaped bi-colored flowers with large white centers and purplish blue petals.

3) Profuse flowering.

4) Each plant carries 10–12 and more upright flower stems each of which carries 12–15 and more flowers.

5) Long lasting, non-dropping flowers.

6) Vigorous and compact grower.

7) Plant saleable 9 to 10 weeks after potting.

8) Seed capsules push slightly through.

9) Medium green, heart-shaped leaves.

10) After maturity the flowers dry off, and remain on the peduncle without becoming infected by botrytis.

The new cultivar is most similar to 'Van Gogh', for which a U.S. plant patent is also in the process of being applied for. Both cultivars have the same unique bi-colored designs on the blossoms with a large white center and another color on the petals. However, 'Van Gogh' has dark lilac petals whereas 'Monet' has purplish blue and somewhat smaller petals.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn.

Botanical classification: *Saintpaulia ionantha*, Ramat., c.v. Monet.

Parentage:

*Male parent.*—1065.

*Female parent.*—735.

Propagation: The new cultivar holds its distinguishing characteristics through successive propagations by leaf cuttings.

Plant: From 8 cm to 10 cm tall when grown in pots, and 24–28 cm in diameter when fully grown.

*Leaves.*—General form: Oval to heart-shaped. Diameter: 60–70 mm wide and 70–80 mm long. Texture: Velvety. Aspect: Slightly serrated, hairy, slightly shiny. Veins: Upperside; visible: underside: well pronounced, light green, shiny. Color (upperside): Yellow-green group 147 A. Color (underside): Greyed-green group 194 D with occasional touches of Greyed-purple group 186 C to D. Petiole: Strong, light green, hairy.

*Flowers.*—Buds: Bell-shaped, greenish and purplish blue, 5–7 mm just before opening. Sepals: Five (5). Color: Green with purplish brown touch. Calyx: Shape: Funnel-shaped. Aspect: Spear-shaped, hairy.

Peduncle: Character: Strong upright, hairy. Color: Green, occasionally brownish touch.

*Individual flowers.*—Size: 35–40 mm. Shape: Single violet-shaped with slightly wavy petal tips. Color (upperside): White center with petals being between violet group 88 B and violet-blue 89 C. Under cooler temperatures and more intensive lighting, the purplish blue tends to intensify. Color (underside): White center with violet group 88 B to C on petals. Borne: Each flower stem carries 12–15 and more flowers on strong, upright peduncles that are free standing above the leaves, thereby forming a compact bouquet. Flowering habit: Flowers 9–10 weeks after potting.

*Reproductive organs.*—Stamens: Two (2). Anthers: 2 composed of 4 anther cells, seed capsules push slightly through. Filaments: Yellowish white, 3–4 mm long. Pollen color: Yellow group 7 A. Styles: 7–8 mm long, purplish blue, base of ovary light green and hairy.

*Roots.*—Normally developed, white when young, turning slightly brownish when older.

Disease resistance: Up to date. 'Monet' has shown very good resistance to all major violet diseases.

General observations:

'Monet' is an attractive cultivar due to its bi-colored flowers which have unique markings of large white centers contrasting with purplish blue petals. The amount of purplish blue spread may vary just slightly from one blossom to another. A tight bouquet of flowers free standing above the leaves develops 9–10 weeks after potting. Each of the 10–12 and more strong flower stems carries 12–15 and more single violet-shaped flowers with slightly wavy petal tips. Medium green, oval to heart-shaped leaves surround the flower bouquet. The flowers are long-lasting and non-dropping and the seed capsules push slightly through.

I claim:

1. A new and distinct cultivar of African violet plant named 'Monet', as described and illustrated, and particularly characterized by its single violet-shaped, multi-colored flowers with unique markings of large white centers contrasting with the purplish blue petals; strong, upright flower stems that curve slightly toward the center to form a compact bouquet above the leaves; medium green, oval to heart-shaped leaves; profuse flowering; vigorous and compact growth habit; flowering 9–10 weeks after potting, and by its long lasting and non-dropping flowers.

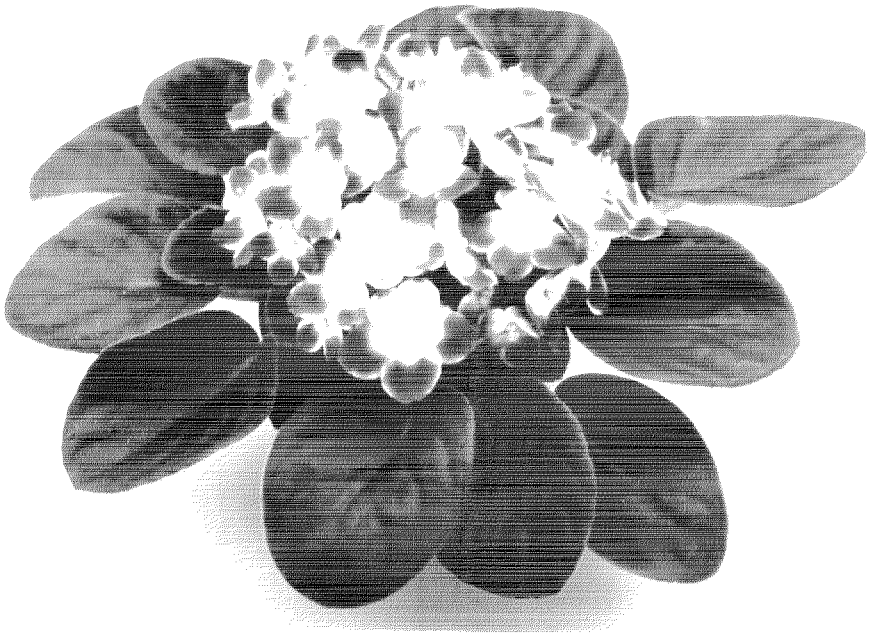

* * * * *